(12) United States Patent
Sauer et al.

(10) Patent No.: US 7,983,462 B2
(45) Date of Patent: Jul. 19, 2011

(54) METHODS AND SYSTEMS FOR IMPROVING QUALITY OF AN IMAGE

(75) Inventors: Ken David Sauer, South Bend, IN (US); Charles Addison Bouman, West Lafayette, IN (US); Jiang Hsieh, Brookfield, WI (US); Jean-Baptiste Thibault, Milwaukee, WI (US)

(73) Assignees: Purdue Research Foundation, West Lafayette, IN (US); General Electric Company, Schenectady, NY (US); The University of Notre Dame du Lac, Notre Dame, IN (US)

( * ) Notice: Subject to any disclaimer, the term of this patent is extended or adjusted under 35 U.S.C. 154(b) by 1038 days.

(21) Appl. No.: 11/284,448

(22) Filed: Nov. 22, 2005

(65) Prior Publication Data

US 2007/0116343 A1    May 24, 2007

(51) Int. Cl.
*G06K 9/00* (2006.01)
*A61B 8/00* (2006.01)

(52) U.S. Cl. .................. 382/131; 382/132; 600/440

(58) Field of Classification Search .......... 382/128–132, 382/173–174; 378/4, 8, 15, 18, 901
See application file for complete search history.

(56) References Cited

U.S. PATENT DOCUMENTS

| | | | |
|---|---|---|---|
| 3,573,623 A | | 4/1971 | Bannon et al. |
| 5,594,767 A * | | 1/1997 | Hsieh ............................ 378/8 |
| 5,680,426 A | | 10/1997 | Ching-Ming |
| 6,343,936 B1 * | | 2/2002 | Kaufman et al. .......... 434/262 |
| 6,514,082 B2 * | | 2/2003 | Kaufman et al. .......... 434/262 |
| 6,678,399 B2 * | | 1/2004 | Doi et al. ..................... 382/131 |
| 6,768,782 B1 | | 7/2004 | Hsieh et al. |
| 6,898,303 B2 * | | 5/2005 | Armato et al. .............. 382/131 |
| 6,907,102 B1 * | | 6/2005 | Sauer et al. ..................... 378/19 |
| 6,970,585 B1 * | | 11/2005 | Dafni et al. .................. 382/131 |
| 7,194,117 B2 * | | 3/2007 | Kaufman et al. ........... 382/128 |
| 7,202,663 B2 * | | 4/2007 | Huang ......................... 324/307 |
| 7,372,934 B2 * | | 5/2008 | De Man et al. ................... 378/4 |
| 2004/0264625 A1 * | | 12/2004 | Basu et al. ..................... 378/4 |

OTHER PUBLICATIONS

Klingensmith et al, "Segmentation of three-dimensional intravascular ultrasound images using spectral analysis and a dual active surface model", 2004 IEEE International Ultrasonics, Ferroelectrics, and Frequency Control Joint 50th Anniversary Conference.*

Bortfeld et al, "Methods of image reconstruction from projections applied to conformation radiotherapy", Phys. Med. Biol., 1990, vol. 35, No. 10, 1423-1434.*

Jean-Baptiste Thibault, Ken Sauer, Charles Bouman and Jiang Hsieh, GE Medical Systems, "High Quality Iterative Image Reconstruction for Multi-Slice Helical CT" (4 pgs.), 2003.

Jiang Hsieh, Applied Science Laboratory, GE Medical Systems, Milwaukee, WI 53201 "Adaptive Edge Enhancement Based on Image Segmentation," SPIE, vol. 3034, (pp. 393-402), 1997.

* cited by examiner

*Primary Examiner* — Vu Le
*Assistant Examiner* — Andrae S Allison
(74) *Attorney, Agent, or Firm* — Armstrong Teasdale LLP

(57) ABSTRACT

A method for improving quality of an image is described. The method includes reconstructing a first image of a sample volume, segmenting the first image to generate a first region and a second region, reconstructing a second image of the sample volume, and generating a final image from a combination of the segmentation, the first image, and the second image.

16 Claims, 3 Drawing Sheets

METHODS AND SYSTEMS FOR IMPROVING QUALITY OF AN IMAGE

BACKGROUND OF THE INVENTION

This invention relates generally to medical imaging systems and more particularly to systems and methods for improving quality of an image.

A computed tomography (CT) imaging system typically includes an x-ray source that projects a fan-shaped x-ray beam through an object, such as a patient, being imaged to a multi-slice array of radiation detectors. The beam is collimated to lie within an X-Y plane, generally referred to as an "imaging plane". Intensity of radiation from the beam received at a detector array is dependent upon attenuation of the beam by the object. Attenuation measurements from each detector element of the detector array are acquired separately to produce a transmission profile.

The x-ray source and the detector array are rotated within a gantry and around the object to be imaged so that a projection angle at which the x-ray beam intersects the object constantly changes. A group of x-ray attenuation measurements and/or projection data, from the detector array at one gantry angle is referred to as a "view". A "scan" of the object includes a set of views made at different projection angles. To perform a helical scan, a table controller moves a table, on which the object is located, parallel to an axis in synchronization with a rotation of the gantry, while the detector array collects the projection data.

One method for reconstructing an image from the projection data is a filtered back projection (FBP). The image is likely to be used for both soft-tissue pathology and bony structure investigation. FBP converts the projection data from a scan into an integer called a CT number or Hounsfield unit (HU), which is used to control brightness of a corresponding pixel on a cathode ray tube display. FBP provides good image quality and computational efficiency.

Iterative reconstruction (IR) is also used for the reconstruction of the image. An advantage of IR is that IR accurately models the projection data. The accurate modeling applies to the CT imaging system with the multi-slice detector array and capable of conducting the helical scan because the CT imaging system produces the projection data that pass obliquely through a plurality of two-dimensional (2-D) reconstructed image planes. By more accurately modeling the projection data, IR can produce reconstructions with higher quality, lower noise, and fewer artifacts. Although IR produces the image with significantly reduced noise in a soft-tissue region, the image in a bony region is generally not as sharp as the bony region in the image reconstructed using FBP. The difference in the sharpness is mainly caused by a factor, such as a nonlinear nature of a regularization, a dependence of a spatial resolution on a spatial location, an image frequency content, and a local contrast level. The factor may result in a lower detail or contrast in the bony region compared to the soft tissue region.

BRIEF DESCRIPTION OF THE INVENTION

In one aspect, a method for improving quality of an image is described. The method includes reconstructing a first image of a sample volume, segmenting the first image to generate a first region and a second region, reconstructing a second image of the sample volume, and generating a final image from a combination of the segmentation, the first image, and the second image.

In another aspect, a processor is described. The processor is configured to reconstruct a first image of a sample volume, segment the first image to generate a first region and a second region, reconstruct a second image of the sample volume, and generate a final image from a combination of the segmentation, the first image, and the second image.

In yet another aspect, an imaging system is described. The imaging system includes an x-ray source configured to generate x-rays, a detector configured to detect the x-rays and generate projection data from the x-rays, and a processor. The processor is configured to reconstruct a first image, of a sample volume, from the projection data, segment the first image to generate a first region and a second region, reconstruct a second image of the sample volume, and generate a final image from a combination of the segmentation, the first image, and the second image.

DETAILED DESCRIPTION OF THE INVENTION

Figure 1:
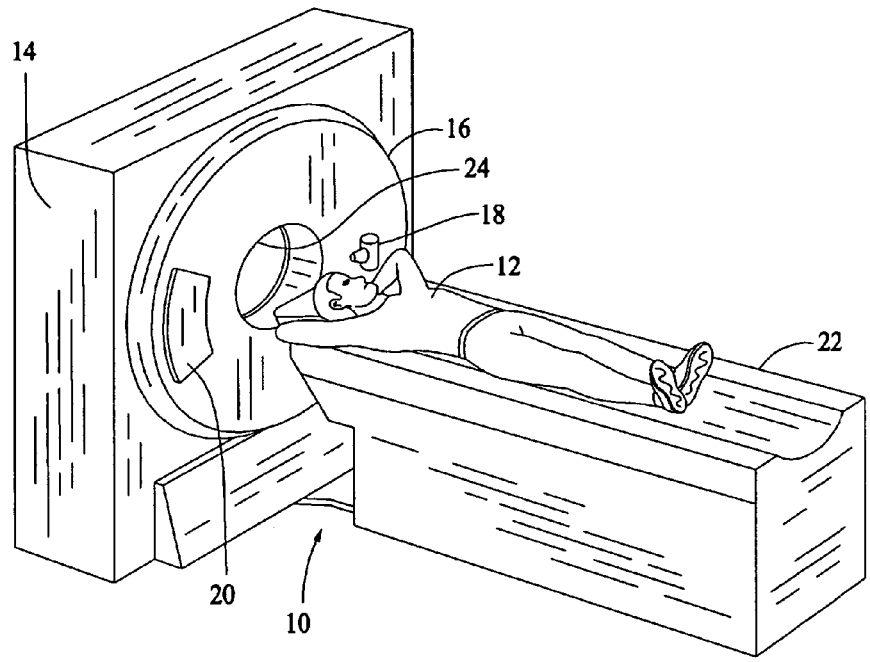
FIG. 1 is an isometric view of an embodiment of a multi-slice computed tomography (CT) imaging system, in which methods and systems for improving quality of an image are implemented.

FIG. 1 is an isometric view of an embodiment of a multi-slice computed tomography (CT) imaging system 10, in which systems and methods for improving quality of an image of a sample volume of a medical patient 12 is implemented. CT imaging system 10 includes a gantry 14 including a rotating inner portion 16. The rotating inner portion 16 includes an x-ray source 18 and a detector array 20. CT imaging system 10 further includes a translatable table 22.

X-ray source 18 projects a beam of x-rays towards detector array 20. X-ray source 18 and detector array 20 rotate about an operably translatable table 22. Translatable table 22 is translated along an axis between x-ray source 18 and detector array 20 to perform either an axial scan or a helical scan. Translatable table 22 translates to move patient 12 inside and outside a bore 24. The beam of x-rays, after passing through patient 12, within the patient bore 24, is detected at detector array 20 to generate raw data. The raw data is pre-processed by a pre-processor to generate projection data that is used to create a CT image. The pre-processing includes, but is not limited to, an offset correction, a primary speed correction, a reference channel correction, and an air-calibration.

Figure 2:
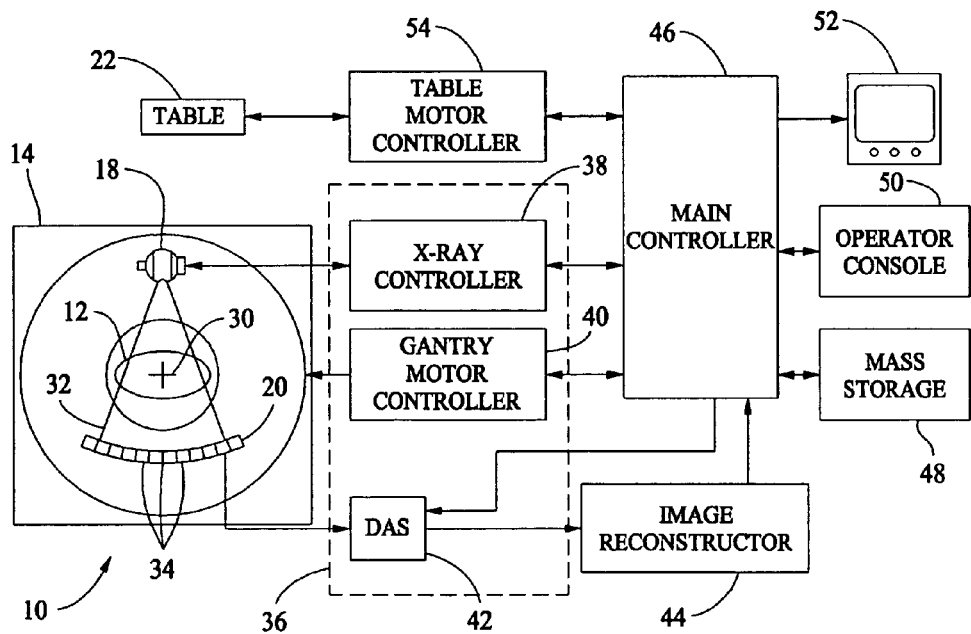
FIG. 2 is a block diagram of an embodiment of the CT imaging system of FIG. 1.

FIG. 2 is a block diagram of an embodiment of CT imaging system 10. CT imaging system 10 includes an x-ray controller 38, a gantry motor controller 40, an image reconstructor 44, a data acquisition system (DAS) 42, a main controller 46, a mass storage device 48, an operator console 50, a display monitor 52, and a table motor controller 54. Each of x-ray controller 38, gantry motor controller 40, image reconstructor 44, main controller 46, and table motor controller 54 is not limited to just those integrated circuits referred to in the art as a controller, but broadly refers to a computer, a processor, a microcontroller, a microcomputer, a programmable logic controller, an application specific integrated circuit, and/or any other programmable circuit. Examples of mass storage device 48 include a nonvolatile memory, such as a read only memory (ROM), and a volatile memory, such as a random access memory (RAM). Other examples of mass storage device 48 include a floppy disk, a compact disc—ROM (CD-ROM), a magneto-optical disk (MOD), and a digital versatile disc (DVD). Display monitor 52 may be a cathode ray tube (CRT) or alternatively a liquid crystal display (LCD).

X-ray source 18 and detector array 20 rotate about a center axis 30. The beam of x-rays 32 is received by multiple detector elements 34 in multiple detector rows. Each detector element 34 generates an electrical signal corresponding to an intensity of beam 32. As beam 32 passes through patient 12, beam 32 is attenuated. Rotation of inner portion 16 of gantry 14 and the operation of x-ray source 18 are governed by a control mechanism 36. Control mechanism 36 includes x-ray controller 38 that provides power and timing signals to x-ray source 18. Control mechanism 36 also includes gantry motor controller 40 that controls a rotational speed and position of inner portion 16. DAS 42 samples analog data from the detector elements 34 and converts the analog data to digital signals for subsequent processing. Image reconstructor 44 receives sampled and digitized x-ray data from the DAS 42 and performs image reconstruction to generate the CT image. Examples of the image reconstruction include filtered back-projection (FBP) and iterative reconstruction (IR).

In FBP, the projection data is weighted and filtered. During backprojection, a scanned area of the sample volume corresponding to a reconstruction field-of-view (RFOV) is utilized from the projection data. In FBP, backprojection is not performed on remaining scanned area outside the RFOV.

In FBP, the CT image is generated from the projection data, which is obtained by pre-processing the raw data. The projection data, representing a plurality of linear integrals of a plurality of attenuation coefficients of patient 12, is filtered. Upon filtering the projection data, the backprojection process, which maps a location of an image element, such as a pixel, to the projection data and accumulates contributions from the projection data that intersect the image element, is performed to obtain the CT image. FBP is described in Avinash C. Kak and Malcolm Slaney, "Principles of Computerized Tomographic Imaging," Classics in Applied Mathematics, 33, SIAM, 2001, ISBN:089871494X.

An image space includes a set of image vectors arranged in an image array. The image array may be of any number of dimensions, such as, two-dimensional, three-dimensional, or alternatively four-dimensional. An example of the image space is a set of all possible images representable on a lattice of a given dimension. One of a plurality of image elements and/or one of the image vectors of the set of the image space may be viewed on display monitor 52 to allow the operator to gain information of an interior of the sample volume.

The forward projection includes a transformation from the image space for the sample volume to a projection space for the sample volume. The forward projection is performed on the image vectors.

The projection space includes a set of projection vectors of integral x-ray attenuation values, which is the projection data. The projection vectors that make the projection space include the projection data. Also, the projection vectors that make up the projection space may be forward projections of the image vectors from the image space.

In IR, forward projection samples based on the CT image are compared with the projection data that is measured. A difference between the forward projection samples and the projection data is used as a basis for updating the CT image. As an example, in IR, image reconstructor 44 determines a cross-section reconstruction vector, which approximately matches the projection data via a CT model as shown in equation 1 as, $$p_n = G(\hat{s}, \theta_n, z_n) \quad (1)$$

In performing IR, CT imaging system 10 is modeled by the function $p_n = G(\hat{s}, \theta_n, z_n)$ that describes expected output of each detector element 34 at each rotation angle $\theta$ and z position. Vector $\hat{s}$ includes a three-dimensional reconstruction of a portion of patient 12 in a plane of reconstruction. Values of vector $\hat{s}$ are determined from known values of $p_n$, $\theta_n$, and $z_n$. Rotation angles $\theta_n$, and positions $z_n$ correspond to the projection data from an $n^{th}$ detector element 34. The projection data $p_n$ and expected values $G(\hat{s}, \theta_n, z_n)$ are compared for each $n^{th}$ detector element 34. To determine the vector $\hat{s}$, image reconstructor 44 determines a contribution of each of the image elements of the image space to each point of the projection data. The vector $\hat{s}$ is determined such that equation 1 is satisfied, or in other words, the vector $\hat{s}$ is determined that approximately matches the projection data. The IR is performed using a technique selected from at least one of a maximum a-posteriori technique, an expectation-maximization technique, and an ordered subsets technique.

The maximum a-posteriori technique measures an optimality of the CT image by applying a cost function including both a term measuring a match of a forward projected image, formed by the forward projection, to the projection data, and a term penalizing departure of the CT image from expected behavior. The maximum a-posteriori technique is discussed in T. Hebert and R. Leahy, "A Generalized EM Algorithm for 3-D Bayesian Reconstruction from Poisson data Using Gibbs Priors," IEEE Transactions on Medical Imaging, vol. 8 no. 2, pp. 194-202, June 1989, K. Sauer and C. A. Bouman, "A Local Update Strategy for Iterative Reconstruction from Projections," IEEE Transactions on Signal Processing, vol. 41, no. 2, pp. 534-548, February 1993, and C. A. Bouman and K. Sauer, "A Unified Approach to Statistical Tomography Using Coordinate Descent Optimization," IEEE Transactions on Image Processing, vol. 5, no. 3, pp. 480-492, March 1996.

The expectation-maximization technique refers to a numerical method, elucidated in A. Dempster, N. Laird and D. Rubin, "Maximum Likelihood from Incomplete Data via the EM Algorithm," Journal of the Royal Statistical Society B, vol. 1 no. 39, pp. 1-38, 1977, L. Shepp and Y. Vardi, "Maximum Likelihood Reconstruction for Emission Tomography," IEEE Transactions on Medical Imaging, vol. MI-1, no. 2, pp. 113-122, October 1982, K. Lange and R. Carson, "EM Reconstruction Algorithms for Emission and Transmission Tomography," Journal of Computer Assisted Tomography, vol. 8 no. 2, pp. 306-316, April 1984, and T. Hebert and R. Leahy, "A Generalized EM Algorithm for 3-D Bayesian Reconstruction from Poisson data Using Gibbs Priors," IEEE Transactions on Medical Imaging, vol. 8 no. 2, pp. 194-202, June 1989.

Main controller 46 stores the CT image in mass storage device 48. Main controller 46 also receives commands and scanning parameters from an operator via an operator console 50. Display monitor 52 allows an operator to observe the CT image and other data from main controller 46. Operator supplied commands and parameters are used by the main controller 46 in operation of DAS 42, x-ray controller 38, and gantry motor controller 40. In addition, main controller 46 operates table motor controller 54, which translates table 22 to position patient 12 in gantry 14.

Figure 3:
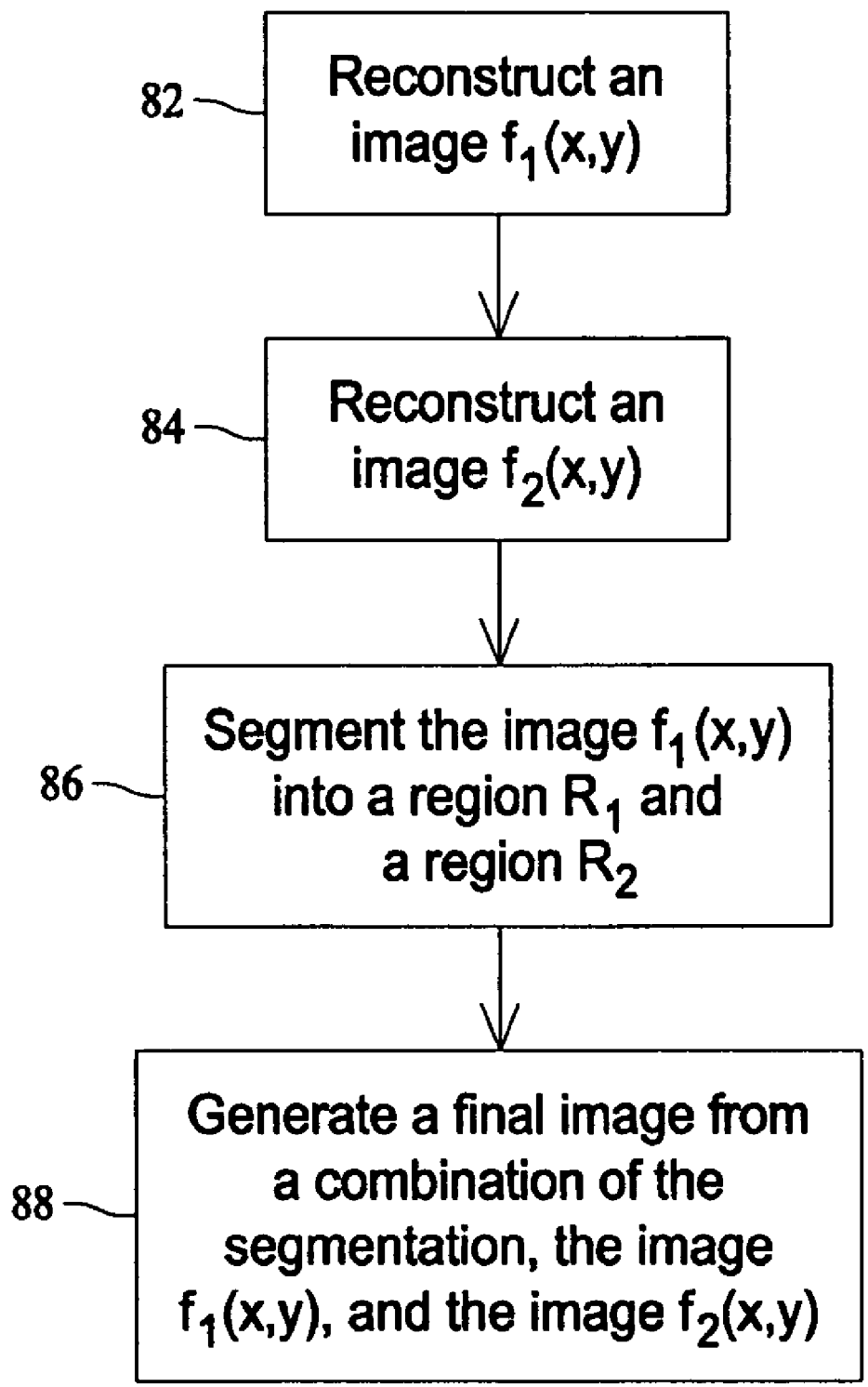
FIG. 3 is a flowchart of an embodiment of a method for improving quality of an image.

FIG. 3 is a flowchart of an embodiment of a method for improving quality of an image. Image reconstructor 44 reconstructs 82 an image $f_1(x,y)$, which is an example of the CT image, by applying one of FBP and IR, where x and y are coordinates of the image space. Image reconstructor 44 reconstructs 84 an image $f_2(x,y)$, which is another example of the CT image, by applying one of FBP and IR. When image reconstructor 44 determines that the image $f_1(x,y)$ has been reconstructed 82 by applying FBP, the image reconstructor 44 reconstructs 84 the image $f_2(x,y)$ by applying IR. Alternatively, when image reconstructor 44 determines that the image $f_1(x,y)$ has been reconstructed 82 by applying IR, the image reconstructor 44 reconstructs 84 the image $f_2(x,y)$ by applying FBP.

Image reconstructor 44 segments 86 the image $f_1(x,y)$ into a region $R_1$ and a region $R_2$. An example of the region $R_1$ is a region that represents a bone of the sample volume. An example of the region $R_2$ is a region that represents a soft tissue, such as muscles or fat, or the sample volume. Image reconstructor 44 segments 86 the image $f_1(x,y)$ by generating a classifier $c(x,y)$. The classifier $c(x,y)$ is generated by applying an equation (2), which is $$c(x, y) = \begin{cases} 0, & f_1(x, y) < \mu_{low} \\ \frac{\mu - \mu_{low}}{\mu_{high} - \mu_{low}}, & \mu_{low} \leq f_1(x, y) < \mu_{high} \\ 1, & f_1(x, y) \geq \mu_{high} \end{cases} \quad (2)$$

where $\mu_{low}$ is a low CT number, which is a low threshold, $\mu_{high}$ is a high CT number, which is a high CT number, $\mu$ is a CT number of one of the image elements, of the image $f_1(x,y)$, at a position (x,y) within the image space. An example of $\mu_{low}$ is 150 and an example of $\mu_{high}$ is 250. The low CT number and the high CT number are provided by the operator via the operator console 50 to image reconstructor 44. Alternatively, the low and high CT numbers are generated algorithmically based on a nature of the CT image. In yet another alternative embodiment, the low and high CT numbers are pre-stored in mass storage device 48. A value of $c(x_1,y_1)$ between zero and 1 provides a probability whether one of the image elements $f_1(x_1,y_1)$, of the image $f_1(x,y)$, at a location $(x_1,y_1)$ is within the region $R_1$ or alternatively within the region $R_2$. For example, when $c(x,y)=q/10$, such as 7/10, image reconstructor 44 determines that there is a (q×10) percent chance that $f_1(x_1,y_1)$ is within a region represent a bone within the image $f_1(x,y)$, where q is a real number between 0 and 10. When $q \geq 5$, image reconstructor 44 determines that $f_1(x_1,y_1)$ is within the region $R_1$ and when q<5, image reconstructor 44 determines that $f_1(x_1,y_1)$ is within the region $R_2$. Alternatively, when q>5, image reconstructor 44 determines that $f_1(x_1,y_1)$ is within the region $R_1$ and when $q \leq 5$, image reconstructor 44 determines that $f_1(x_1,y_1)$ is within the region $R_2$. When $c(x_1,y_1)=1$, image reconstructor 44 determines that $f_1(x_1,y_1)$ is within the region $R_1$. When $c(x_1,y_1)=0$, image reconstructor 44 determines that $f_1(x_1,y_1)$ is within the region $R_2$.

A low pass filter within image reconstructor 44 low pass filters the classifier $c(x,y)$ to generate an additional classifier $c'(x,y)$. The low pass filter removes high frequency components from the classifier $c(x,y)$ to reduce an impact of noise to the segmentation. An example of the low pass filter includes a convolution filter, which convolves the classifier $c(x,y)$ with known convolution masks. Another example of the low pass filter includes a filter that averages the classifier $c(x,y)$. For instance, the low pass filter averages the classifier $c(x,y)$ by generating an average of $c(x_1,y_1)$ and $c(x_2,y_2)$, where $c(x_1,y_1)$ is the classifier of the location $(x_1,y_1)$ and $c(x_2,y_2)$ is the classifier of a location $(x_2,y_2)$ within the image $f_1(x,y)$. As yet another example, the low pass filter includes a boxcar smoothing filter, where each CT number is replaced by an average of a number of nearest neighbors, including the CT number, of the CT number. Another example of the low pass filter includes a Gaussian shaped filter. Yet another example of the low pass filter includes a median filter that generates a median of the classifier $c(x,y)$. As an example, the median filter generates a median value of $c(x_1,y_1)$, $c(x_2,y_2)$, and $c(x_3,y_3)$, where $c(x_3,y_3)$ is the classifier at a location $(x_3,y_3)$ within the image $f_1(x,y)$.

The low pass filter low pass filters the additional classifier $c'(x,y)$ to generate another additional classifier $c''(x,y)$. The other additional classifier $c''(x,y)$ is generated to reduce an impact of a sharp transition within the image $f_1(x,y)$ and to create intermediate values at a transition boundary within the image $f_1(x,y)$. As an example, the sharp transition includes a transition in which the other additional classifier $c''(x,y)$ changes from zero to one. In the example, the low pass filter performs low pass filtering to satisfy $0<c''(x_4,y_4)<c''(x_5,y_5)<1$, where $c''(x_4,y_4)$ is the other additional classifier at a location $(x_4,y_4)$ within the image $f_1(x,y)$ and $c''(x_5,y_5)$ is the other additional classifier at a location $(x_5,y_5)$ within the image $f_1(x,y)$.

Image reconstructor 44 generates 88 a final image $f(x,y)$ from a combination of the image $f_1(x,y)$, the image $f_2(x,y)$, and the classifier $c(x,y)$ by applying an equation $$f(x,y)=c(x,y) \cdot f_1(x,y)+[1-c(x,y)] \cdot f_2(x,y) \quad (3)$$

where $1-c(x,y)$ is a complement of the classifier $c(x,y)$. In an alternatively embodiment, image reconstructor 44 generates the final image $f(x,y)$ by applying an equation $$f(x,y)=c'(x,y) \cdot f_1(x,y)+[1-c'(x,y)] \cdot f_2(x,y) \quad (4)$$

In yet another alternative embodiment, image reconstructor 44 generates the final image $f(x,y)$ by applying an equation $$f(x,y)=c''(x,y) \cdot f_1(x,y)+[1-c''(x,y)] \cdot f_2(x,y) \quad (5)$$

By applying any one of equations (3), (4), and (5), a region, such as a region representing a bone of the sample volume, within the image $f_2(x,y)$ is replaced by a corresponding region, such as representing the bone, of the image $f_1(x,y)$. In an alternatively embodiment, image reconstructor 44 does not apply the low pass filter to generate the additional classifier $c'(x,y)$ and does not apply equation (4). In yet another alternative embodiment, image reconstructor 44 does not apply the low pass filter to generate the other additional classifier $c'(x,y)$ and does not apply equation (5).

Image reconstructor 44 scales down a contribution made by the image $f_1(x,y)$ to the final image $f(x,y)$ by reducing the other additional classifier $c''(x,y)$ according to $$c_s(x,y)=\alpha \cdot c''(x,y) \quad (6)$$

where $\alpha$ is a scaling factor, $0 < \alpha \leq 1$, and $c_s(x,y)$ is a scaled classifier. The scaling down is performed when the operator or alternatively the image reconstructor 44 determines that a level of noise within the image $f_1(x,y)$ is high. Image reconstructor 44 determines that a level of noise within the image $f_1(x,y)$ is high by measuring a variance of a plurality of CT numbers within the image $f_1(x,y)$ and determining that the variance is above a pre-determined value provided by the operator via the operator console 50. The scaling down is performed to blend the image $f_2(x,y)$, and to achieve a compromise between a spatial resolution within the image $f_2(x,y)$ and noise within the image $f_2(x,y)$. The scaling down is not performed when the operator or alternatively the image reconstructor 44 determines that a level of noise within the image $f_1(x,y)$ is low. Image reconstructor 44 determines that a level of noise within the image $f_1(x,y)$ is low by measuring the variance of a plurality of CT numbers within the image $f_1(x,y)$ and determining that the variance is below the predetermined value provided by the operator via the operator console 50. When the image reconstructor 44 or alternatively the operator determines not to scale down the other additional classifier $c''(x,y)$, image reconstructor 44 does not apply equation (6). Image reconstructor 44 generates the final image $f(x,y)$ by applying an equation $$f(x,y) = c_5(x,y) \cdot f_1(x,y) + [1-c_5(x,y)] \cdot f_2(x,y) \qquad (7)$$

Image reconstructor 44 changes a value of a parameter σ, used to penalize the image elements, based on the other additional classifier $c''(x,y)$. Image reconstructor 44 changes the value of the parameter σ to sharpen a representation of regions representing a bone within the image $f_2(x,y)$. Image reconstructor 44 increases the value of the parameter σ to an increased amount that is input by the operator via the operator console 50. Image reconstructor 44 increases the value of the parameter σ to the increased amount when the image reconstructor 44 determines that the image elements, at the location (x,y) for which $c''(x,y)$ is calculated and within the image $f_2(x,y)$, are in a region representing a bone of the sample volume. Image reconstructor 44 decreases the value of the parameter σ to a decreased amount that is input by the operator via the operator console 50. Image reconstructor 44 decreases the value of the parameter σ to the decreased amount when the image reconstructor 44 determines that the image elements, at the location (x,y) for which $c''(x,y)$ is calculated and within the image $f_2(x,y)$, are in a region representing a soft tissue of the sample volume. The increased value is greater than the decreased value.

Image reconstructor 44 applies the parameter σ in a penalty function provided by $$S(x) = \sum_{\{x_1,x_2\} \in N} b_{x_1-x_2} \rho\left(\frac{f_2(x_1) - f_2(x_2)}{\sigma}\right) \qquad (8)$$

where σ is a convex function, $f_2(x_1)$ is a CT number of the one of the image elements at the location xi within the image $f_2(x,y)$, $f_2(x_2)$ is a CT number of one of the image elements at the location $x_2$ within the image $f_2(x,y)$, and $b_{x_1-x_2}$ is a parameter. As an example, $b_{x_1-x_2}$ is a distance between the locations $x_1$ and $x_2$. Image reconstructor 44 adjusts the parameter σ based on the difference $f_2(x_1)-f_2(x_2)$. For example, when the difference $f_2(x_1)-f_2(x_2)$ is greater than a pre-determined amount provided by the operator via the operator console 50, image reconstructor 44 decreases the difference by a specific amount that is also specified by the operator via the operator console 50. As another example, when the difference $f_2(x_1)-f_2(x_2)$ is lesser than the pre-determined amount, image reconstructor 44 increases the difference by a certain amount that is also specified by the operator via the operator console 50.

The penalty function can be applied to the locations $y_1$ and y2 within the image space by replacing $x_1$ by $y_1$, and replacing $x_2$ by y2 in the equation (8). In an alternative embodiment, the penalty function is applied to two dimensions within the image space according to $$S(x) = \sum_{\{(x_1,y_1),(x_2,y_2)\} \in N} b_{x_1-x_2,y_1-y_2} \rho\left(\frac{f_2(x_1,y_1) - f_2(x_2,y_2)}{\sigma}\right) \qquad (9)$$

where $b_{x_1-x_2,y_1-y_2}$ is a distance between the locations $(x_1, y_1)$ and $(x_2,y_2)$, $f_2(x_1,y_1)$ is a CT number of one of the image elements at the location $(x_1,y_1)$, and $f_2(x_2,y_2)$ is a CT number of one of the image elements at the location $(x_2,y_2)$.

In an alternative embodiment, image reconstructor 44 applies the equations (2), (3), (4), and (5) after replacing the image $f_1(x,y)$ in equations (2), (3), (4), and (5) with an image $f_b(x,y)$ optimized for a bone of the sample volume and applies the equations (2), (3), (4), and (5) after replacing $f_2(x,y)$ in equations (2), (3), (4), and (5) with an image $f_s(x,y)$ optimized for a soft tissue of the sample volume. Image reconstructor 44 reconstructs the image $f_b(x,y)$ by reconstructing the image $f_1(x,y)$, determining, from a CT number, that one of the image elements represents a bone of the sample volume, and applying IR to the image element determined. One of the image elements representing a bone of the sample volume has a CT number at least equal to a threshold input via the operator console 50 by the operator. Alternatively, image reconstructor 44 reconstructs the image $f_b(x,y)$ by reconstructing the image $f_1(x,y)$, determining from the other additional classifier $c''(x, y)$, one of the image elements representing a bone of the sample volume, and applying the penalty function. When image reconstructor 44 determines that the other additional classifier $c''(x,y)$ is at least equal to a predefined amount, the image reconstructor 44 determines that one of the image elements represents a bone of the sample volume. When image reconstructor 44 determines that the other additional classifier $c''(x,y)$ is greater than a predefined amount, the image reconstructor 44 applies the penalty function to obtain the image $f_b(x,y)$ by increasing the value of the parameter σ to an amount input by the operator via the operator console 50.

Image reconstructor 44 reconstructs the image $f_s(x,y)$ by reconstructing the image $f_1(x,y)$, determining, from a CT number, that one of the image elements represents a soft tissue of the sample volume, and applying IR to the image element. One of the image elements representing a soft tissue of the sample volume has a CT number lesser than the threshold input via the operator console 50 by the operator. Alternatively, image reconstructor 44 reconstructs the image $f_s(x, y)$ by reconstructing the image $f_1(x,y)$, determining from the other additional classifier $c''(x,y)$, one of the image elements representing a soft tissue of the sample volume, and applying the penalty function. When image reconstructor 44 determines that the other additional classifier $c''(x,y)$ is lesser than the predefined amount, the image reconstructor 44 determines that one of the image elements represents a soft tissue of the sample volume. When image reconstructor 44 determines that the other additional classifier $c''(x,y)$ is lesser than the predefined amount, image reconstructor 44 applies the penalty function to obtain the image $f_s(x,y)$ by decreasing the value of the parameter σ to an amount input by the operator via the operator console 50. The CT image generated using IR has a good ability to suppress noise and a robust result is generated by replacing $f_1(x,y)$ in equations (2), (3), (4), and (5) with the image $f_b(x,y)$ and replacing $f_2(x,y)$ in equations (2), (3), (4), and (5) with the image $f_s(x,y)$.

Figure 4:
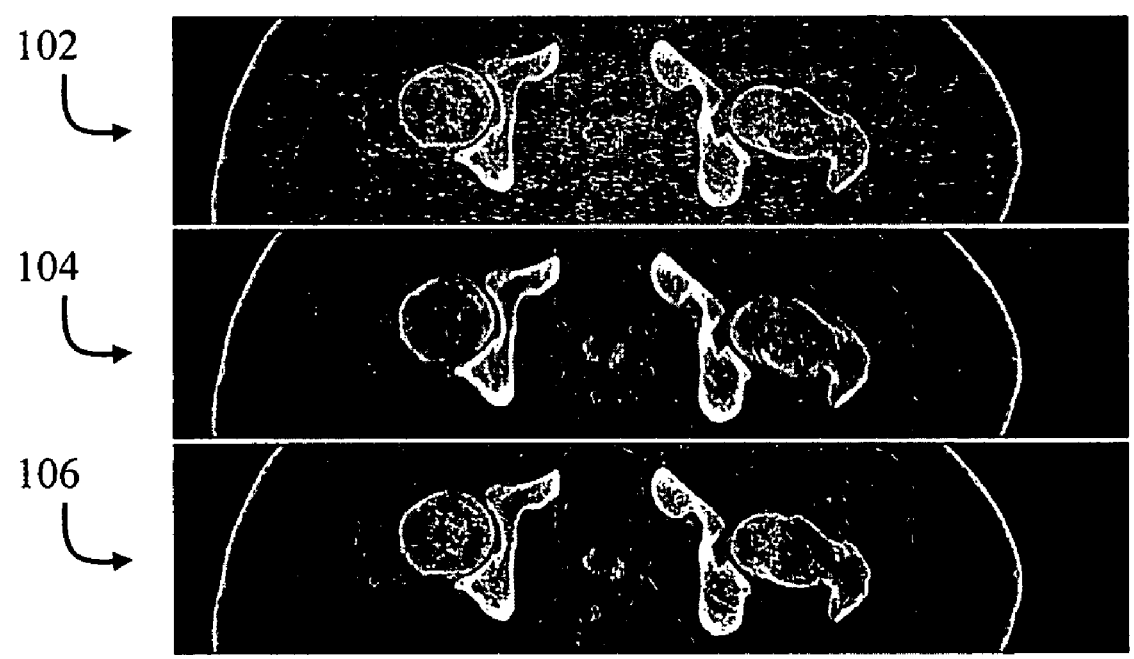
FIG. 4 shows an embodiment of a plurality of images representing an effect of applying the method illustrated in FIG. 3.

FIG. 4 shows an embodiment of a plurality of images 102, 104, and 106. Image 102 is reconstructed by applying FBP, image 104 is reconstructed by applying IR, and image 106 is reconstructed by applying the systems and methods for improving quality of an image. Image 106 provides resolution, such as sharpness, of bones represented within image 102 and low noise characteristics, such as, smoothness, of soft tissues represented within image 104.

It is noted that the systems and methods for improving quality of an image can be applied within other imaging systems, such as, a positron emission tomography (PET)

imaging system, a CT-PET imaging system, a magnetic resonance imaging (MRI) imaging system, or an ultrasound imaging system. Examples of the CT-PET imaging system include a Discovery LS PET-CT system commercially available from General Electric™ Medical Systems, Waukesha, Wis. Another example of the CT-PET imaging system includes a Discovery ST system commercially available from General Electric™ Medical Systems.

Technical effects of the herein described systems and methods for improving quality of an image include reducing a sharp contrast between a bony region and a soft tissue region of patient 12 without applying an advanced regularization. Other technical effects include producing superior noise properties in the soft tissue region while maintaining a sharpness in the bony region.

While the invention has been described in terms of various specific embodiments, those skilled in the art will recognize that the invention can be practiced with modification within the spirit and scope of the claims.

What is claimed is:

1. A method for improving quality of an image, said method comprising:
    reconstructing a first image of a sample volume by performing a first image reconstruction method;
    generating a classifier using a computed tomography number of an image element within the first image;
    segmenting the first image into a first region and a second region using the generated classifier, wherein the first image reconstruction method is selected based at least in part on the computed tomography numbers of image elements within the first region;
    reconstructing a second image of the sample volume by performing a second image reconstruction method, wherein the second image reconstruction method is different than the first image reconstruction method and selected based at least in part on the computed tomography numbers of image elements within the second region; and
    generating a final image by combining the second image and one of the first region and the second region of the first image, the final image at least one of stored on a computer readable media, transmitted from a data acquisition system for further processing, and displayed to a user.

2. A method in accordance with claim 1 wherein said reconstructing the first image comprises reconstructing the first image by one of filtered backprojection and iterative reconstruction and said reconstructing the second image comprises reconstructing the second image by the other of filtered backprojection and iterative reconstruction.

3. A method in accordance with claim 1 wherein said generating the final image comprises generating the final image from a combination of the first image, the second image, and the classifier.

4. A method in accordance with claim 1 wherein said generating the final image comprises generating the final image from a combination of the first image, the second image, the classifier, and a complement of the classifier.

5. A method in accordance with claim 1 wherein said generating the final image comprises generating the final image from a sum of a multiplication of the classifier with the first image and a multiplication of a complement of the classifier with the second image.

6. A method in accordance with claim 1 further comprising low pass filtering the classifier at least once to generate an additional classifier.

7. A method in accordance with claim 1 further comprising applying a median filter to the classifier.

8. A method in accordance with claim 1 further comprising low pass filtering the classifier at least once to generate an additional classifier, and wherein said generating the final image comprises generating the final image from a combination of the first image, the second image, and the additional classifier.

9. A method in accordance with claim 1 wherein the first region comprises a region representing bones of the sample volume and the second region comprises a region representing soft tissues of the sample volume.

10. A method in accordance with claim 1 further comprising:
    optimizing a representation of a bone, of the sample volume, represented within the first image; and
    optimizing a representation of a soft tissue, of the sample volume, represented within the second image, wherein said generating a classifier using a computed tomography number of an image element within the first image comprises generating a classifier from a computed tomography number of an image element within the optimized representation of the bone, and said generating the final image comprises generating the final image from the optimized representation of the bone, the optimized representation of the soft tissue, and the classifier.

11. A method in accordance with claim 1 further comprising low pass filtering the classifier at least once to generate an additional classifier and adjusting, based on a value of the additional classifier, a parameter used to penalize an image element within the second image.

12. A processor configured to:
    reconstruct a first image of a sample volume by performing a first image reconstruction method;
    generate a classifier from a computed tomography number of an image element within the first image;
    segment the first image into a first region and a second region based on the classifier, wherein the first image reconstruction method is selected based at least in part on the computed tomography numbers of image elements within the first region;
    reconstruct a second image of the sample volume by performing a second image reconstruction method, wherein the second image reconstruction method is different than the first image reconstruction method and selected based at least in part on the computed tomography numbers of image elements within the second region; and
    generate a final image by combining the second image and one of the first region and the second region of the first image.

13. A processor in accordance with claim 12 wherein the processor reconstructs the first image by applying one of filtered backprojection and iterative reconstruction and reconstructs the second image by applying the other of filtered backprojection and iterative reconstruction.

14. A processor in accordance with claim 12 wherein the processor is configured to generate the final image from a combination of the first image, the second image, and the classifier.

15. An imaging system comprising:
    an x-ray source configured to generate x-rays;
    a detector configured to detect the x-rays and generate projection data from the x-rays; and
    a processor configured to:
        reconstruct a first image, of a sample volume, from the projection data by performing a first image reconstruction method;
        generate a classifier from a computed tomography number of an image element within the first image;

segment the first image into a first region and a second region based on the classifier, wherein the first image reconstruction method is selected based at least in part on the computed tomography numbers of image elements within the first region;

reconstruct a second image of the sample volume by performing a second image reconstruction method, wherein the second image reconstruction method is different than the first image reconstruction method and selected based at least in part on the computed tomography numbers of image elements within the second region; and generate a final image by combining the second image and one of the first region and the second region of the first image.

16. An imaging system in accordance with claim 15 wherein the processor reconstructs the first image by applying one of filtered back projection and iterative reconstruction and reconstructs the second image by applying the other of filtered backprojection and iterative reconstruction.

* * * * *